United States Patent [19]

Haber et al.

[11] Patent Number: 5,231,993
[45] Date of Patent: Aug. 3, 1993

[54] BLOOD SAMPLER AND COMPONENT TESTER WITH GUIDE MEMBER

[75] Inventors: Terry M. Haber, Lake Forest; William H. Smedley, Lake Elsinore, both of Calif.

[73] Assignee: Habley Medical Technology Corporation, Laguna Hills, Calif.

[21] Appl. No.: 795,133

[22] Filed: Nov. 20, 1991

[51] Int. Cl.⁵ .............................................. A61B 5/00
[52] U.S. Cl. .................................. 128/770; 606/181; 206/569
[58] Field of Search ................ 128/763, 770, 760, 762, 128/767, 743; 606/181, 182, 167, 185; 206/568, 569, 570, 363, 365, 366, 367

[56] References Cited

U.S. PATENT DOCUMENTS

| | | | |
|---|---|---|---|
| 3,741,197 | 6/1973 | Sanz et al. | 606/182 |
| 4,375,815 | 3/1983 | Burns | 606/182 |
| 4,379,456 | 4/1983 | Cornell et al. | 606/182 |
| 4,462,405 | 7/1984 | Ehrlich | 606/182 |
| 4,635,633 | 1/1987 | Hufnagle | 606/181 |
| 5,014,718 | 5/1991 | Mitchen | 128/771 |
| 5,047,044 | 9/1991 | Smith et al. | 606/182 |
| 5,054,499 | 10/1991 | Swierczek | 128/770 |
| 5,059,394 | 10/1991 | Phillips et al. | 422/68.1 |
| 5,100,427 | 3/1992 | Crossman et al. | 606/182 |

FOREIGN PATENT DOCUMENTS

| | | | |
|---|---|---|---|
| 3515420 | 10/1986 | Fed. Rep. of Germany | 128/770 |
| 2590673 | 5/1987 | France | 128/763 |

OTHER PUBLICATIONS

"Instructions for the Auto-Lancet", Palco Laboratories, 1595 Soquel Drive, Santa Cruz, CA 95065, no date.
Photocopy of package, ExacTech TM Blood Glucose Meter, Baxter Travernol Laboratories, Inc. Deerfield, Ill. 60051, no date.
Photocopy of package, ExacTech TM Blood Glucose Test Strips, Medisense, no date.
Photocopy of package insert, ExacTech TM, no date.
Photocopy of package insert, Glucofilm TM Normal Control, Miles, Inc., Sept., 1989.
Photocopy of package insert, Glucofilm TM test strips, Miles, Inc. Diagnostics Division, Elkhart, IN 46515 no date.

Primary Examiner—Max Hindenburg
Assistant Examiner—Guy V. Tucker
Attorney, Agent, or Firm—Townsend & Townsend Khourie & Crew

[57] ABSTRACT

A reagent strip (10) and lance (6) are integrated to form a blood sampler and component tester (2). The reagent strip (10) is adapted for application against the skin of a patient and carries a reagent that indicates the concentration of a blood component in a blood sample placed in contact therewith. The lance (6), which is used to pierce the skin of a patient, is coupled to the reagent strip (10) through a resilient dome (4) which translates the lance between an extended position (where the lance through a guide member (20) extends beyond the reagent strip to puncture the skin of a patient) and a retracted position.

22 Claims, 2 Drawing Sheets

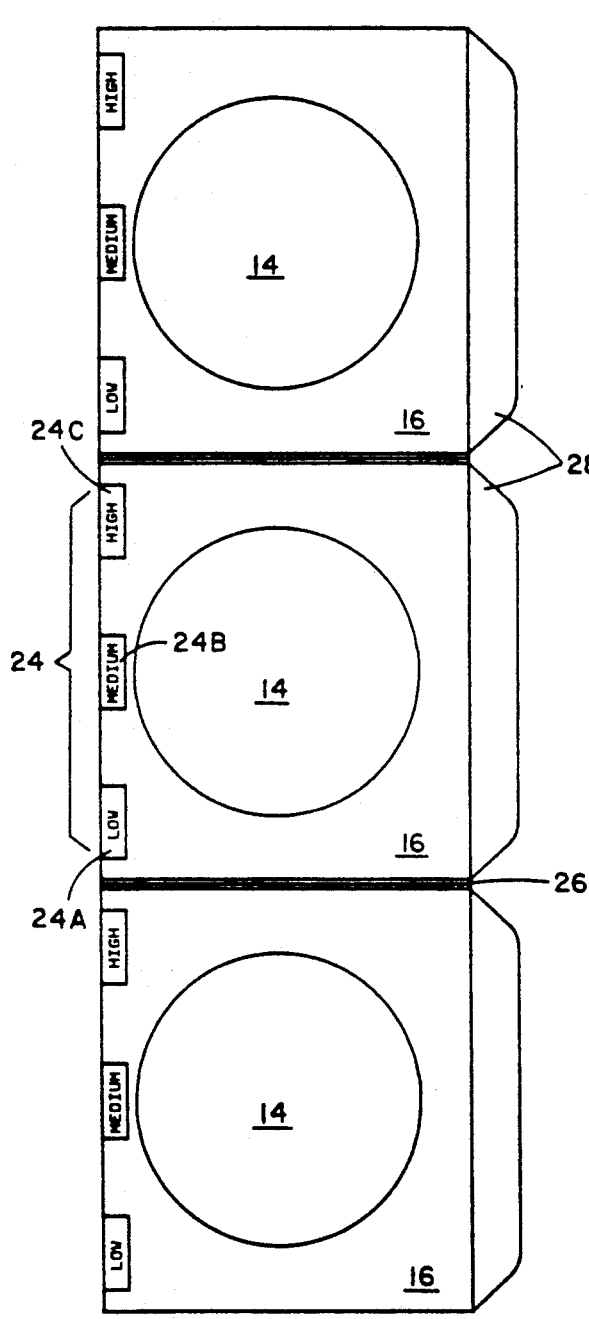
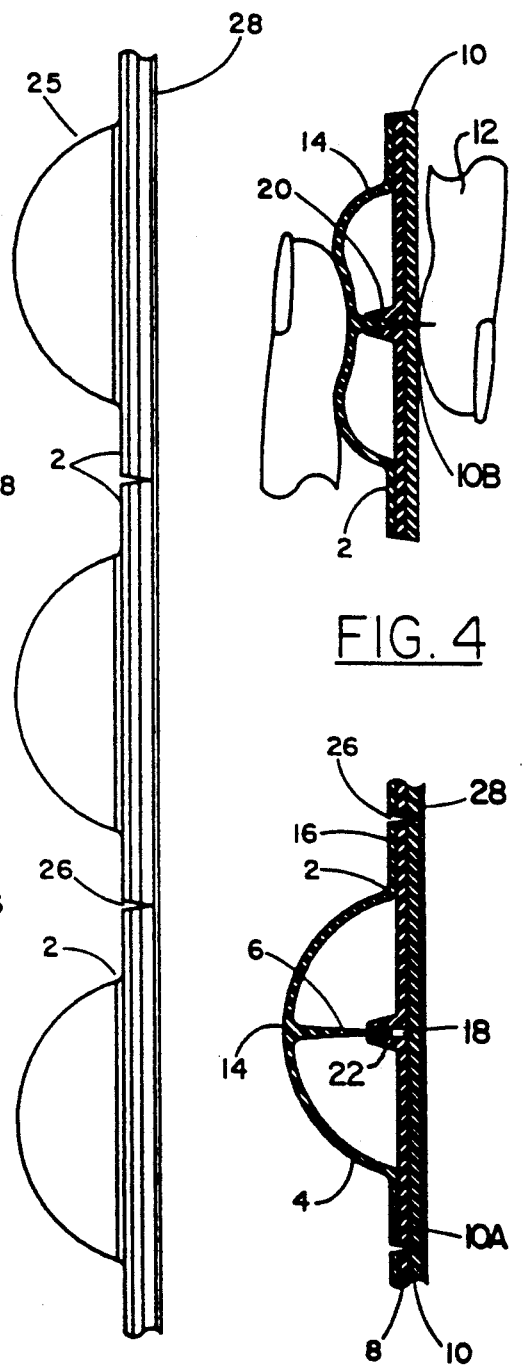
FIG. 1    FIG. 2    FIG. 3

BLOOD SAMPLER AND COMPONENT TESTER WITH GUIDE MEMBER

BACKGROUND OF THE INVENTION

The present invention relates to blood component testing generally, and more particularly to blood glucose level testing devices.

Heretofore, various methods have been developed to carry out a program of home glucose monitoring for diabetics. These methods typically require a piercing device for piercing the skin of the patient to obtain a capillary blood sample and a separate device or mechanism for testing the concentration of glucose in the sample. Typically, automatic lancets, which include a generally complex arrangement of elements that cooperate to automatically trigger and retract a needle (lance), are used to pierce the skin. During use, the tip of the automatic lancet is placed lightly against the chosen site on a finger of a patient. A trigger is actuated which causes the lance to penetrate the skin. Some of these lancets are constructed such that the lance immediately retracts inside the lancet after making the skin puncture. Then the automatic lancet is lifted away from the finger and put aside, while a large drop of blood is allowed to form at the puncture site. One way in which the blood sample is tested is with what is known as a test strip. These test strips generally include reagents which when placed in contact with the blood sample undergo a change in color that indicates the glucose level of the sample. One such test strip is made by Miles, Inc., Diagnostic Div., Elkhart, Ind. and marketed under the name Glucofilm TM. These strips are typically stored in a bottle to avoid contamination.

When removing a test strip from its bottle, the user must be careful not to use the hand which has been pierced with the lancet. Otherwise, the blood sample could be lost from the pierced finger. The strip is placed on a flat dry surface with the target area of the strip (i.e., the reagent area) facing upward. The punctured finger is then positioned such that the blood forms a hanging drop which will naturally spread over the target area on contact. A proper size drop forms a small dome that completely covers the target. It is also important that the user not smear the blood sample onto the test strip or cover the area of the test strip that surrounds the reagent with the blood sample. Otherwise, inaccurate blood glucose level readings can result.

One of the drawbacks of the procedure described above is that it is awkward. Once the lance has been actuated to puncture a chosen site on the finger, only one hand is available to put aside the automatic lancet, obtain a test strip and position that strip such that a blood sample can be properly deposited thereon.

In addition, the number of component elements used to carry out the method creates inventory problems. For example, the user must maintain a supply of lances for the automatic lancet and a supply of test strips. If the lancet or one of these supply items is unavailable, the patient's glucose level cannot be monitored. This can happen by inadvertently forgetting to pack the automatic lancet or an appropriate supply of lances or test strips when preparing for overnight or extended travel.

Therefore, there is a need to provide a system for testing blood glucose levels that permits the procedure to be easily and reliably carried out. The system also should simplify inventory requirements.

SUMMARY OF THE INVENTION

The present invention is directed to a device for testing the concentration of a blood component in a blood sample that avoids the problems and disadvantages of the prior art. The invention generally accomplishes this goal by providing a modular construction that integrates a reagent carrying member and a lance. The reagent carrying member is adapted for application against the skin of a patient and contains a reagent that indicates the concentration of a blood component in a blood sample placed in contact therewith. The lance, which is used to pierce the skin of a patient, is coupled to the reagent carrying member through a mechanism that translates the lance between a first position where the distal end of the lance is positioned on one side of the pad and a second position where the distal end of the lance is positioned on the other side of the reagent carrying member for puncturing the patient's skin.

The integrated construction eliminates the need for complicated and relatively expensive automatic lancets, loading and unloading lancets with replacement lance darts, and maintaining a separate supply of test strips for testing the blood sample. In addition, with the integrated lance and reagent carrying member construction, blood flows directly from the finger to the reagent carrier, thereby eliminating complications that can arise with conventional methods of placing a drop of the blood sample on a test strip.

Another feature of the invention is that a plurality of the modular sampler-testers can be interconnected in series to form a roll or strip of testers. The number of modules in a given strip can be selected to provide the user with a supply of testers sufficient for two weeks, a month, etc. A modular tester is simply torn from the roll when the blood is to be tested.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 is a top plan view of the blood sampler and component tester in accordance with the principles of the present invention;

FIG. 2 is a side elevational view of the invention illustrated in FIG. 1;

FIG. 3 is a longitudinal cross section of the invention illustrated in FIG. 1 showing the lance in the retracted state;

FIG. 4 is a longitudinal cross section of the invention illustrated in FIG. 1 showing the lance in the extended state;

FIG. 5 is a bottom plan view of the invention illustrated in FIG. 1, while FIGS. 5a and 5b are views taken along line 5—5 showing a first and second embodiment of the invention;

DESCRIPTION OF THE PREFERRED EMBODIMENTS

Figure 7:
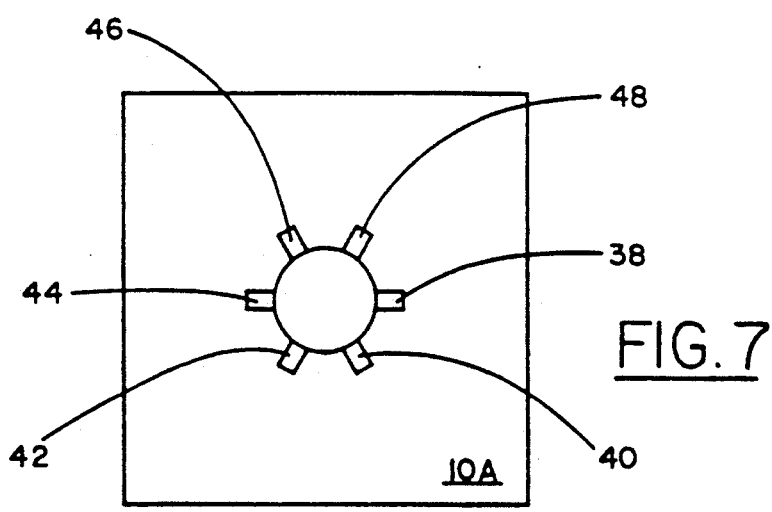
FIG. 7 is a bottom plan view of a further embodiment of the invention illustrated in FIG. 1.

Referring to the drawings in detail, wherein like numerals indicate like elements, the blood sampler and component tester is illustrated in accordance with the principles of the present invention. Although the sampler and tester will be described with respect to blood glucose testing, the invention can be constructed to test other blood components as will be apparent from the following description, drawings and appended claims.

FIGS. 1 and 2 illustrate the modular construction of each integrated blood sampler and tester. Referring to FIG. 3, each module 2 includes a dome-shaped member 4 having a piercing element or lance 6 which is arranged to pass through substrate 8 and reagent strip 10 to puncture the skin of a patient's finger 12 such that a sampling of blood can be made (FIG. 4). Dome-shaped member 4 includes a cup-shaped or convex portion 14 and a generally flat or planar portion 16. Piercing element or lance 6 extends from the central region of cup-shaped portion 14 and is preferably integrally formed therewith, for example, by molding.

Dome-shaped member 4 is attached to generally planar substrate 8 by securing generally planar portion 16 of the dome-shaped member to one side of the substrate. This can be done in a way conventional to those skilled in the art. For example, generally flat portion 16 of the dome-shaped member can be adhesively secured, ultrasonically welded or fused with heat to substrate 8. During manufacture, a plurality of dome-shaped members 4 can be molded to form a plurality of serially connected domes 4 which can then be attached in mass to an appropriate length of substrate.

Referring to FIGS. 3 and 4, substrate 8 has a central opening 18 for permitting lance 6 to readily pass through the substrate, which preferably is plastic. Substrate 8 further includes a guide member 20 for guiding lance 6 through opening 18 in substrate 8. Guide member 20 is illustrated in the form of a hub member that is integrally formed with the substrate such that central aperture 22 in hub member 20 is aligned with central opening 18 in the substrate. Reagent strip 10, preferably comprising paper, also can be provided with a hole to enhance the smooth passage of lance 6 therethrough.

Hub member 20 also functions as a stop mechanism for limiting rectilinear translation of lance 6. It is important that the lance does not extend beyond reagent strip 10 and, thus, into the patient's finger more than about 0.06 inches. One way in which the extension of lance 6 is limited is illustrated in FIG. 4. In that figure, the lateral dimension of the central aperture 22 of hub member 20 is less than the lateral dimension of lance 6 in the region adjacent to the interior surface of cup-shaped member 14. It should be understood that other ways to limit the translation and, thus, the penetration of lance 6 can be used without departing from the scope of the invention.

Figures 5, 5A, 5B:
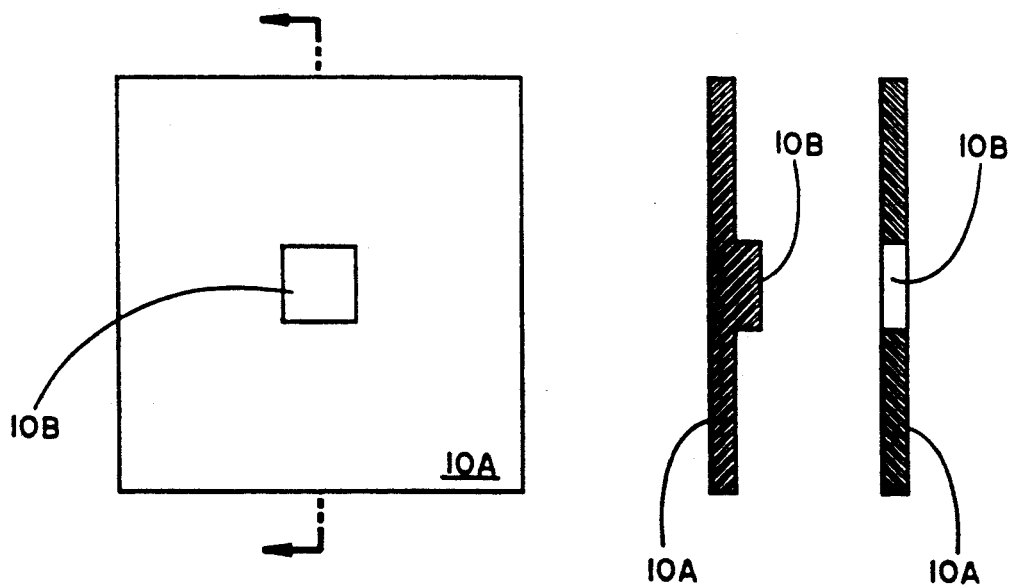

Referring to FIGS. 4 and 5, reagent strip 10 includes generally planar carrier 10a and reagent pad 10b. One surface 30 of carrier 10a is adhesively or mechanically attached to the side of substrate 8 opposite dome-shaped member 4. The other surface, i.e., the exposed surface of carrier 10a supports reagent containing pad 10b which is attached (e.g., adhesively or mechanically) to the exposed surface of carrier 10a (FIG. 5a). Reagent pad 10b contains a reagent that indicates the concentration of glucose in a blood sample placed in contact therewith. When the reagent pad is placed in contact with a blood sample, the reagent pad changes color or hue according to glucose concentration in the blood sample. Accordingly, the pad and strip composition and construction can be similar to commercially available test strips for blood glucose testing such as Glucofilm ™ strips discussed above. Such test strips use standard enzymes such as peroxidase (horseradish) and glucose oxidase, and standard color enzyme substrates such as tetramethylbenzidine. Generally, the glucose oxidase catalyzes the oxidation of glucose in the blood sample, producing gluconic acid and hydrogen peroxide. In the presence of peroxidase, the hydrogen peroxide oxidizes the tetramethylbenzidine turning the test pad blue with an intensity proportional to the glucose concentration. Other reagents can be used to produce other color changes as is conventional to those of ordinary skill in the art.

Alternatively, the reagent pad can be embedded or encapsulated in reagent strip 10 (FIG. 5b). As evident from FIG. 5b, reagent pad 10b extends the entire thickness of carrier 10a. This construction is advantageous for reasons discussed below. It also should be noted that carrier 10a can be impregnated with reagent. In this way, the reagent also can be applied such that it is present throughout the entire thickness of the carrier.

A color code is provided to interpret the meaning of the reagent color change. Thus, the color code can include regions of different hue for a particular color. Referring to FIG. 1, segments 24a, 24b and 24c can, for example, represent light, medium and dark shades of a particular color, wherein these shades indicate low, normal and high glucose levels. With this arrangement, when the reagent matches light segment 24a in the color code, the glucose level is low and insulin is needed. But when the reagent matches the relatively dark segment 24c of the color code, the glucose level is high which indicates that the diet of the patient should be more carefully monitored.

The color code is shown on the top marginal surface of generally flat portion 16. This position is especially advantageous when dome-shaped member 4 and substrate 8 comprise transparent material such as clear plastic. When this construction is used in conjunction with a reagent pad that extends the entire thickness of the reagent strip (e.g., a pad embedded in the strip as illustrated in FIG. 5), the user can simultaneously view and compare the reagent color and color code. Alternatively, the color code can be provided on the substrate beneath transparent convex portion 14 of dome-shaped member 4. However, when dome-shaped member 4 and substrate 8 are not transparent, the color preferably is attached to the exposed undersurface of reagent strip 10.

FIG. 2 illustrates a strip 25 of serially connected blood sampler and testing modules 2. The strip contains a supply of modules sufficient for monitoring blood glucose level over the selected period of time. A mechanically weakened portion, tear line 26, extends in the transverse direction of the strip between adjacent modules so that the modules may be separated for use. In this way, the user can simply tear off the terminal or desired number of modules from the strip along the tear line. Although the tear line is shown in FIG. 2 in the form of a groove that extends through dome-shaped member 4, substrate 8 and reagent strip 10, other conventional techniques can be used to provide a mechanically weakened portion that facilitates separation of the modules. For example, a perforated region that extends transversely between adjacent modules can be used in lieu of tear line 26.

The method for using the disposable blood sampler and component tester will be described with reference to FIGS. 3 and 4. First, the user simply tears off a blood sampler and tester module 2 along tear line 26 to separate a module from the supply strip. Then sterile strip 28, which seals and protects reagent strip 10 from contamination, is peeled off. Sterile strip 28 is releasably secured to reagent strip 10 by adhesive and can be in the form of conventionally known protective strips such as the protective strips used on Band-Aids ® which are bandages manufactured by Johnson & Johnson. Once the protective strip 28 has been removed, module 2 is placed on the patient's finger such that the reagent strip 10 is in contact with the patient's skin. The convex portion of dome-shaped member 4 is depressed, thereby causing lance 6 to slide through guide 20 and central opening 18 in substrate 8, and puncture the skin of the patient (FIG. 3). As soon as the puncture is made, the patient immediately lifts the finger that was used to actuate the device (FIG. 4). The dome of dome-shaped member 4 immediately pops back to its original position illustrated in FIG. 3, thereby rapidly retracting lance 3 from the patient's finger. The configuration of dome-shaped member 4, together with its thickness and composition ensures that the dome portion 14 will rapidly spring back to its original position. In other words, the construction of dome-shaped member 4 and its connection with substrate 8 provides the dome-shaped member with a natural bias that urges lance 6 toward the retracted state. It has been found that a dome comprising polypropylene and having a diameter of about 0.60–1.00 inches, a wall thickness of about 0.060–0.080 inches and a radius of curvature of about 1.20 inches provides the desired results. After the blood has sufficiently contacted the reagent pad through capillary flow, the user can then compare the color or hue of the reagent pad to the color code to the glucose level of the blood sample. The modular sampler and tester can be discarded after use.

Electronic sensors can be used to provide a more accurate reading of the glucose concentration in the blood sample. Such sensors, which electronically measure the glucose level, are commercially available such as the ExacTech ™ blood glucose sensor distributed by Baxter Travenol Laboratories, Inc. These devices enable those who are visually impaired, such as the color blind, to carry out glucose monitoring at home. However, these sensors are relatively expensive and can be misplaced or lost. Further embodiments of the present invention which are illustrated in FIGS. 6 and 7, provide a simple and relatively inexpensive mechanism integrated with the module to facilitate blood glucose monitoring by those with certain visual impairments such as color blindness.

Figure 6:
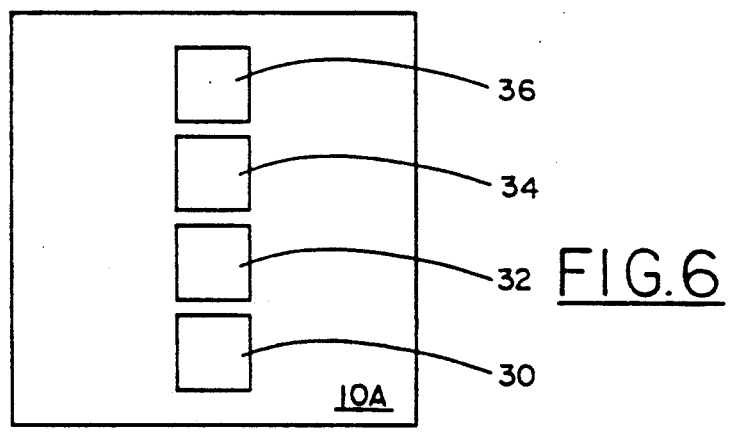
FIG. 6 is a bottom plan view of another embodiment of the invention illustrated in FIG. 1.

Referring to FIG. 6, a plurality of reagent regions or pads are arranged linearly. Each reagent pad 30, 32, 34 and 36 is doped with different reagent concentrations. By varying the concentration of the enzymes, or more preferably the color enzyme substrate, one can alter the color density for a given reaction. For example, pad 30 can contain a reagent concentration that undergoes a sharp change in hue when exposed to a low concentration of glucose in a blood sample. Pads 32, 34 and 36 can be doped with reagent concentrations such that these pads sequentially undergo a sharp change in hue as the concentration of glucose in the blood sample increases. Since each sharp change in hue effectively corresponds to an on-off signal, pads 30-36 can be doped to indicate to an individual who is color blind whether his/her glucose level is in a range below normal, normal or above normal. Furthermore, by increasing the number of pads to a number greater than three (the number of ranges), greater precision in measuring glucose concentration can be achieved. For example, when pad 30 undergoes a sharp change in hue (on-position) and the remaining pads do not undergo any change in hue (off-position), an extremely low glucose level could be indicated. On the other hand, when both pads 30 and 32 undergo a sharp change in hue and pads 34 and 36 remain unchanged (the off-position), the code could represent a sensed glucose level that is very close to normal.

Although one arrangement is described above with reference to FIG. 6, it should be understood that any other arrangement can be used which incorporates the above-discussed principles. By way of example, FIG. 7 illustrates a further embodiment of the invention showing another arrangement of reagent pads 38, 40, 42, 44, 46 and 48. Again, these pads are doped with different reagent concentrations such that different on-off combinations of the pads indicate different concentrations of glucose in the blood sample.

The above is a detailed description of a particular embodiment of the invention. It is recognized that departures from the disclosed embodiment may be within the scope of the invention and that obvious modifications will occur to a person skilled in the art. The full scope of the invention is set out in the claims that follow and in their equivalents. Accordingly, the claims and specifications should not be construed to unduly narrow the full scope of protection to which the invention is entitled. For example, the term "reagent strip" is chosen to aid disclosure rather than limit the invention, and use of this term is not intended to limit the reagent carrier to a long or narrow piece. This term is used herein to generically describe a reagent carrier of any configuration.

What is claimed is:

1. A device for testing the concentration of a blood component present in a blood sample, said device comprising:

a member adapted for application against the skin of a patient, said member carrying a reagent that indicates the concentration of a blood component in a blood sample placed in contact therewith;

a lance for piercing the skin of a patient, said lance having a proximal end and a distal end;

a flexible dome-shaped member for translating said lance between a first position where the distal end of said lance is positioned on one side of said reagent carrying member and a second position where the distal end of said lance is positioned on another side of said reagent carrying member, said dome-shaped member being coupled to the proximal end of said lance;

a substrate comprising a layer of material that is positioned between said dome-shaped member and said reagent carrying member; and a guide member for guiding said lance through said substrate and said reagent carrying member.

2. The device for testing the concentration of a blood component present in a blood sample of claim 1 further comprising a chart having regions of different hue, whereby the hue of the reagent after the reagent has reacted with a blood sample is compared to at least one of said regions to determine the sugar level of the blood sample.

3. The device of claim 2 wherein said chart and substrate are integrated in a single construction.

4. The device of claim 3 wherein said substrate comprises clear plastic.

5. The device of claim 3 wherein said dome-shaped member and substrate comprise clear plastic.

6. A device for testing the concentration of a blood component present in a blood sample, said device comprising:
   a member adapted for application against the skin of a patient, said member carrying a reagent that indicates the concentration of a blood component in a blood sample placed in contact therewith;
   a lance for piercing the skin of a patient, said lance having a proximal end a distal end; and
   a flexible dome-shaped member for translating said lance between a first position where the distal end of said lance is positioned on one side of said reagent carrying member and a second position where the distal end of said lance is positioned on another side of said reagent carrying member said dome-shaped member being coupled to the proximal end of said lance;
   a substrate comprising a layer of material that is positioned between said dome-shaped member and said reagent carrying member;
   said substrate includes an opening. said opening being aligned with said lance such that said lance extends through said opening when said lance is in said second position; and
   a hub member for guiding said lance through said substrate, said hub member having a central aperture aligned with said opening in said substrate.

7. The device of claim 6 wherein said reagent carrying member comprises paper.

8. The device of claim 6 wherein said reagent comprises a substance that changes color according to the sugar level of a blood sample placed in contact therewith.

9. The device of claim 6 wherein said dome-shaped member and said lance are integrally formed as a single piece.

10. The device of claim 6 wherein said dome-shaped member comprises means for biasing said lance away from said reagent carrying member.

11. The device of claim 6 wherein said dome-shaped member is fixedly secured to said substrate.

12. The device of claim 6 wherein said lance includes a portion having a lateral dimension greater than the corresponding lateral dimension of said central aperture, thereby limiting the length of the lance that can extend beyond said reagent pad when said lance is in said second position.

13. The device of claim 6 further including a protective strip of material releasably secured to said reagent carrying member.

14. The device of claim 6 further including a color code integrated therewith, said color code having regions of different color, whereby the color of the reagent after reaction with a blood sample is compared to at least one of said color regions to determine the sugar level of the blood sample.

15. The device of claim 6 further including a pad that carries at least a portion of said reagent, said pad being coupled to said reagent carrying member.

16. The device of claim 15 wherein said pad is adhesively attached to said reagent carrying member.

17. The device of claim 15 wherein said pad is mechanically attached to said reagent carrying member.

18. The device of claim 15 wherein said pad is embedded in said reagent carrying member.

19. A diagnostic system including a plurality of disposable modules that are coupled in series, each module comprising:
   a member that carries a reagent which changes color according to sugar present in a substance placed in contact therewith;
   an actuator coupled to said reagent carrying member;
   a layer of material positioned between said actuator and said carrying member, said layer of material including an aperture;
   a lance that extends from said actuator in a direction toward said reagent carrying member; and
   means for guiding said lance through said aperture.

20. The system of claim 19 wherein said actuator comprises a member having a flexible convex portion.

21. A method for monitoring blood glucose level in a pate int comprising the steps of:
   providing a module with a carrier carrying a sugar sensitive reagent, a lance movingly mounted relative to the carrier, and a guide member;
   placing the module against the skin of a patient;
   guiding the lance in the guide member toward the carrier;
   reciprocating the lance through the carrier a distance sufficient to puncture the patient's skin and draw a capillary blood sample;
   applying at least a portion of the blood sample to the reagent.

22. The method for monitoring blood glucose level in a patient of claim 21 further comprising the step of comparing the hue of the reagent that has reacted with the blood sample with the different regions of a chart carried by the module to determine the blood glucose level.

* * * * *